United States Patent
Austen et al.

(10) Patent No.: US 8,399,408 B2
(45) Date of Patent: Mar. 19, 2013

(54) METHOD FOR TREATING DIABETES USING NEURTURIN

(75) Inventors: Matthias Austen, Gottingen (DE); Ulrike Burk, Göttingen (DE)

(73) Assignee: DeveloGen Aktiengesellschaft, Gottingen (DE)

( * ) Notice: Subject to any disclaimer, the term of this patent is extended or adjusted under 35 U.S.C. 154(b) by 0 days.

(21) Appl. No.: 13/028,181

(22) Filed: Feb. 15, 2011

(65) Prior Publication Data

US 2011/0256113 A1    Oct. 20, 2011

Related U.S. Application Data

(63) Continuation of application No. 10/580,601, filed as application No. PCT/EP2004/013534 on Nov. 29, 2004, now abandoned.

(30) Foreign Application Priority Data

Nov. 27, 2003 (EP) .................................. 03027383

(51) Int. Cl.
  A61P 3/08    (2006.01)
  A61P 3/10    (2006.01)
  A61K 38/00   (2006.01)
(52) U.S. Cl. .......................... 514/6.8; 514/6.9; 530/300
(58) Field of Classification Search .................. None
  See application file for complete search history.

(56) References Cited

U.S. PATENT DOCUMENTS

| | | | |
|---|---|---|---|
| 5,739,307 A | 4/1998 | Johnson, Jr. et al. | |
| 6,090,778 A | 7/2000 | Johnson, Jr. et al. | |
| 6,274,554 B1 | 8/2001 | Magal et al. | |
| 6,743,628 B1 | 6/2004 | Johnson, Jr. et al. | |
| 2002/0122829 A1 | 9/2002 | Kishino et al. | |
| 2003/0166537 A1 | 9/2003 | Hanke et al. | |
| 2005/0054102 A1 | 3/2005 | Wobus et al. | |
| 2005/0222070 A1 | 10/2005 | Dohrmann et al. | |
| 2008/0241106 A1 | 10/2008 | Austen et al. | |
| 2009/0258829 A1 | 10/2009 | Harder et al. | |
| 2011/0003741 A1 | 1/2011 | Austen et al. | |
| 2011/0277045 A1 | 11/2011 | Dohrmann et al. | |

FOREIGN PATENT DOCUMENTS

| EP | 1 010 432 A | 6/2000 |
|---|---|---|
| WO | WO 97/08196 A | 3/1997 |
| WO | WO 99/06064 A | 2/1999 |
| WO | WO 00/17360 A1 | 3/2000 |
| WO | WO 00/18922 A2 | 4/2000 |
| WO | WO 01/57272 A2 | 8/2001 |
| WO | WO 02/086107 | 10/2002 |
| WO | WO 03/099318 A2 | 12/2003 |
| WO | WO 2004/093804 A1 | 11/2004 |
| WO | WO 2008/000447 A1 | 1/2008 |
| WO | WO 2009/059755 A2 | 5/2009 |

OTHER PUBLICATIONS

Bowie et al., 1990, Science 247: 1306-1310.*
Wells, 1990, Biochemistry 29:8509-8517.*
Airaksinen et al., "The GDNF Family: Signalling, Biological Functions and Therapeutic Value," Nature Reviews, vol. 3, pp. 383-394 (2002).
Atkinson et al., "The NOD mouse model of type 1 diabetes: As good as it gets?," Nature Medicine, vol. 5(6), pp. 601-604 (1999).
Banks, William A., "Characteristics of compounds that cross the blood-brain barrier," BMC Neurology, vol. 9 (Suppl 1): S3, pp. 1-5 (2009).
Benjamin et al., "A plasticity window for blood vessel remodelling is defined by pericyte coverage of the preformed endothelial network and is regulated by PDGF-B and VEGF," Development, vol. 125(9), pp. 1591-1598 (1998).
Bernard-Kargar et al., "Endocrine Pancreas Plasticity under Physiological and Pathological Conditions," Diabetes, vol. 50, Supplement 1, pp. S30-S35 (2001).
Boado, R. J. et al., "Blood-Brain Barrier and New Approaches to Brain Drug Delivery," Conferences and Reviews, The Western Journal of Medicine, vol. 156(3), pp. 281-286 (1992).
Bonner-Weir et al., "The pancreatic ductal epithelium serves as a potential pool of progenitor cells," Pediatric Diabetes, vol. 5, pp. 16-22 (2004).
Bork et al., "Go hunting in sequence databases but watch out for the traps," Trends Genet. vol. 12(10), pp. 425-427 (1996).
Bork, P., "Powers and pitfalls in sequence analysis: the 70% hurdle," Genome Res., vol. 10(4), pp. 398-400 (2000).
Bouwens et al., "Regulation of Pancreatic Beta-Cell Mass," Physiol. Rev., vol. 85, pp. 1255-1270 (2005).
Brun et al., "The Dianetes-linked Transcription factor Pax4 is Expressed in Human Pancreatic Islets and is Activated by Mitogens and GLP-1," Human Molecular Genetics, vol. 17(4), pp. 478-469 (2008).
Carlsten et al., "GDNF and Neurturin Treatment Reverse Deficits in Diabetic Neuropathy," 2001 Neuroscience Meeting Planner, San Diego, CA, Program No. 138.17: Society for Neuroscience, 2001 [Online]. Retrieved on Apr. 21, 2010.
Chen et al., "Reversine Increases the Plasticity of Lineage-committed Mammalian Cells," PNAS, vol. 104(25), pp. 10482-10487 (2007).
Chen et al., "Exploring Stem Cell Biology With Small Molecules," Mol. BioSyst., vol. 2, pp. 18-24 (2006).
Christianson et al., "Restorative Effects of Neurotrophin Treatment on Diabetic-Induced Cutaneous Axon Loss in Mice," Experimental Neurology, vol. 179(2), pp. 188-199 (2003).
D'Amour et al., "Production of Pancreatic Hormone-Expressing Endocrine Cells from Human Embryonic Stem Cells," Nature Biotechnology, vol. 24(11), pp. 1392-1401 (2006).
Doerks et al., "Protein annotation: detective work for function prediction," Trends Genet. vol. 14(6), pp. 248-250 (1998).
Dohrman et al., "Identification of novel differentiation factors for stem-cell based diabetes therapy," 2385-PO, Diabetes, New York, NY, US, vol. 52, No. Suppl 1, XP009042336, p. A550 (2003) abstract.

(Continued)

Primary Examiner — Gyan Chandra
(74) Attorney, Agent, or Firm — Ropes & Gray LLP

(57) ABSTRACT

The present invention relates generally to methods for preventing and/or treating pancreatic disorders, particularly those related to diabetes, by administering a neurturin protein product.

7 Claims, 5 Drawing Sheets

OTHER PUBLICATIONS

Dor et al., "Adult pancreatic β-cells are formed by self-duplication rather than stem-cell differentiation," Nature, vol. 429, pp. 41-46 (2004).
Dor et al., "Facultative Endocrine Progenitor Cells in the Adult Pancreas," Cell, pp. 183-184 (2008).
Edlund, "Pancreatic Organogenesis-Developmental Mechanisms and Implications for Therapy," Nature Reviews, vol. 3. pp. 574-532 (2002).
Guo at al., "Stem Cells to Pancreatic β-Cells: New Sources for Diabetes Cell Therapy," Endocrine Reviews, vol. 30(3), pp. 214-227 (2009).
Hitchcock, S.A. et al., "Structure—Brain Exposure Relationships," Journal of Medicinal Chemistry, vol. 49(26), pp. 7559-7583 (2006).
Ito et al., "Expression of glial cell line-derived neurotrophic factor family members and their receptors in pancreatic cancers," Surgery, vol. 138(4), pp. 788-794 (2005).
Jing et al., "GFRa-3 Are Two New Receptors for Ligands of the GDNF Family," Journal of Biological Chemistry, vol. 272(52), pp. 33111-33117 (1997).
Jomary et al., "Epitope-tagged recombinant AAV vectors for expressing neurturin and its receptor in retinal cells," Molecular Vision, SN, Atlanta, US, vol. 7, pp. 36-41 XP002325005ISSN: 1090-0535 (2001).
Karaca et al., "Exploring Functional β-Cell Heterogeneity in Vivo Using PSA-NCAM as a Specific Marker," PLoS One, vol. 4(5) pp. e5555 (2009).
Kotzbauer et al., "Neurturin, a relative of glial-cell-derived neurotrophic factor," Nature, vol. 384, pp. 467-470, XP002092404ISSN: 0028-0836 (1996).
Kroon et al., "Pancreatic Endoderm Derived From Human Embrytonic Stem Cells Generates Glucose-Responsive Insulin-Secreting Cells in vivo," Nature Biotechnology, vol. 26(4), pp. 443-452 (2008).
Liew et al., "PAX4 Enhances Beta-Cell Differentiation of Human Embryonic Stem Cells", PloS One, vol. 3, issue 3, pp. 1-11 (2008).
Lin et al.. "Enhancement of Insulin-producing Cell Differentiation from Embryonic Stem Cells Using Pax-4-nucleofection Method," World Journal of Gastroenterology, vol. 13(11), pp. 1672-1679 (2007).
Lu et al., "Pax4 Paired Domain Mediates Direct Protein Transduction into Mammalian Cells," Endocrinology, vol. 148(11) pp. 5558-5565 (2007).
Mannucci et al.,"Fasting plasma glucose and glycated haemoglobin in the screening of diabetes and impaired glucose tolerance," Acta Diabetol, vol. 40(4), pp. 181-186 (2003).
Masure et al., "Enovin a Member of the Glial Cell-Line-Derived Neurotrophic Factor (GDNF) Family with Growth Promoting Activity on Neuronal Cells," European Journal of Biochemistry, vol. 266(3), pp. 892-902, XP000882981ISSN: 0014-2956 (1999).
Moore, A., "Advances in beta-cell imaging," European Journal of Radiology, vol. 70(2) pp. 254-257 (2009).
Murray et al., "Differentiation of Embryonic Stem Cells to Clinically Relevant Populations: Lessons from Embryonic Development," Cell, vol. 132, pp. 661-680 (2008).
Mussman et al., "Inhibition of GSK3 Promotes Replication and Survival of Pancreatic Beta Cells," The Journal of Biological Chemistry, vol. 282(16), pp. 12030-12037 (2007).
Noguchi et al., "PDX-1 Protein Containing Its Own Antennapedia-Like Protein Transduction Domain Can Transduce Pancreatic Duct and Islet Cells," Diabetes, vol. 52, pp. 1732-1737 (2003).
Oiwa et al., "Dopaminergic Neuroprotection and Regeneration by Neurturin Assessed by Using Behavioral, Biochemical and Histochemical Measurements in a Model of Progressive Parkinson's Disease," Brain Research, vol. 947, pp. 271-283, XP008056645 (2002).
Oliver-Krasinski et al., "On the origin of the β-cell," Genes & Development, vol. 22, pp. 1998-2021 (2008).
Parkash et al., "The Structure of the Glial Cell Line-derived Neurotrophic Factor-Coreceptor Complex," The Journal of Biological Chemistry, vol. 283(50), pp. 35164-35172 (2008).
Prince et al. "Recent advances in pancreas development: from embryonic pathways to programming renewable sources of beta cells," F1000 Biol Rep. vol. 2(17) pp. 1-4. doi:10.3410/B2-17 (2010).
Risbud and Bhonde, "Models of pancreatic regeneration in diabetes," Diabetes Res Clin Pract., vol. 58, pp. 155-165 (2002).
Rosenblad et al., "Protection and Regulation of Nigral Dopaminergic Neurons by Neurturin or GDNF in a Partial Lesion Model of Parkinson's Disease After Administration into the Striatum or the Laternal Ventricle," European Journal of Neuroscience, vol. 11(5), pp. 1554-1566, XP008055970ISSN: 0953-816X (1999).
Rossi et al., "Parasympathetic Innervation and Function of Endocrine Pancreas Requires the Glial Cell Line-Derived Factor Family Receptor α2 (GFRα2)," Diabetes, vol. 54(5), pp. 1324-1330 (2005).
Sariola et al., "Novel functions and signalling pathways for GDNF," Journal of Cell Science, vol. 116, pp. 3855-3862 (2003).
Shi et al., "A Combined Chemical and Genetic Approach for the Generation of Induced Pluripotent Stem Cells," Cell Stem Cell, vol. 2, pp. 525-528 (2008).
Sigmund C.D., "Viewpoint: Are studies in genetically altered mice out of control?", Arterioscler Thromb Vasc Biol., vol. 20, pp. 1425-1429 (2000).
Skolnick, J. et al., "From genes to protein structure and function: novel applications of computational approaches in the genomicera," Trends Biotechnol., vol. 18(1), pp. 34-39 (2000).
Slack et al., "Developmental biology of the pancreas," Development, vol. 121, pp. 1569-1580 (1995).
Sosa-Pineda et al., "The Pax4 gene is essential for differentiation of insulin-producing b cells in the mammalian pancreas," Nature, vol. 386, pp. 399-402 (1997).
Spence et al. "Translational Embryology: Using Embryonic Principles to Generate Pancreatic Endocrine Cells From Embryonic Stem Cells," Developmental Dynamics, vol. 236, pp. 3218-3227 (2007).
Takahasi et al., "Induction of Pluripotent Stem Cells from Mouse Embryonic and Adult Fibroblast Cultures by Defined Factors," Cell, vol. 126, pp. 663-676 (2006).
Tourrel et al., "Glucagon-Like Peptide-1 and Exendin-4 Stimulate β-Cell Neogenesis in Streptolotocin-treated newborn rats resulting in persistently improved glucose homeostasis at adult age," Diabetes, vol. 50, pp. 1562-1570 (2001).
Tsaniras et al., "Generating Pancreatic β-cells From Embryonic Stem Cells by Manipulating Signaling Pathways," Apr. 2010.
Vukicevic et al., "Induction of nephrogenic mesenchyme by osteogenic protein 1 (bone morphogenetic protein 7)," Proc Natl Acad Sci USA. vol. 93(17), pp. 9021-9026 (1996).
Winter, W.E. and Schatz, D., "Prevention strategies for type 1 diabetes mellitus," Biodrugs, vol. 17(1), pp. 39-64 (2003).
Xu et al., "β Cells Can Be Generated from Endogenous Progenitors in Injured Adult Mouse Pancreas," Cell, vol. 132, pp. 197-207 (2008).
Zhang et al., "The rat model of type 2 diabetic mellitus and its glycometabolism characters," Exp Anim, vol. 52(5), pp. 401-407 (2003).
Zhou et al., "Generation of Induced Pluripotent Stem Cells Using Recombinant Proteins,"Cell Stem Cell, vol. 4, pp. 381-384 (2009).

* cited by examiner

METHOD FOR TREATING DIABETES USING NEURTURIN

This application is a continuation of U.S. application Ser. No. 10/580,601 filed May 25, 2006, which is a national-stage filing under 35 U.S.C. 371 of International Application No. PCT/EP04/13534, filed Nov. 29, 2004, which is based on and claims priority to European Application Serial Number 03027383.3, filed Nov. 27, 2003. The disclosures of each of the foregoing applications are herein incorporated by reference in their entirety.

SEQUENCE LISTING

The instant application contains a Sequence Listing which has been submitted via EFS-Web and is hereby incorporated by reference in its entirety. Said ASCII copy, created on Feb. 15, 2011, is named 1027280038302.txt and is 4,401 bytes in size.

The present invention relates generally to methods for preventing and/or treating pancreatic disorders, particularly those related to diabetes, by administering a neurturin product.

BACKGROUND OF THE INVENTION

The pancreas is an exocrine gland that secretes digestive enzymes directly into the digestive tract as well as an endocrine gland that secretes hormones into the blood stream. The exocrine function is assured by acinar and centroacinar cells that secrete various digestive enzymes via intercalated ducts into the duodenum. The functional unit of the endocrine pancreas is the islet of Langerhans. Islets are scattered throughout the exocrine portion of the pancreas and are composed of four main cell types: alpha-, beta-, delta- and PP-cells (reviewed for example in Kim & Hebrok, 2001, Genes Dev. 15: 111-127). Beta-cells produce insulin, represent the majority of the endocrine cells and form the core of the islets, while alpha-cells secrete glucagon and are located in the periphery. Delta-cells and PP-cells are less numerous and secrete somatostatin and pancreatic polypeptide, respectively. Recently, cells producing the neuropeptide Ghrelin have been found in pancreatic islets (Wierup et al., 2002, Regal Pept. 107:63-9.).

Early pancreatic development has been well studied in different species, including chicken, zebrafish, and mice (for a detailed review, see Kim & Hebrok, 2001, supra). The pancreas develops from distinct dorsal and ventral anlagen. Pancreas development requires specification of the pancreas anlage along both anterior-posterior and dorsal-ventral axes. A number of transcription factors, that are critical for proper pancreatic development have so been identified (see Kim & Hebrok, 2001, supra; Wilson et al., 2003, Mech Dev, 120: 65-80).

In humans, the acinar and ductal cells retain a significant proliferative capacity that can ensure cell renewal and growth, whereas the islet cells become mostly mitotically inactive. This is in contrast to rodents where beta-cell replication is an important mechanism in the generation of new beta cells. It has been suggested, that during embryonic development, pancreatic islets of Langerhans originate from differentiating duct cells or other cells with epithelial morphology (Bonner-Weir & Shama, 2002, J Pathol. 197: 519-526; Cu et al., 2003, Mach Day. 120: 35-43). In adult humans, new beta-cells arise in the vicinity of ducts (Butler at al., 2003, Diabetes 52: 102-110; Bouwens & Pipeleers 1998, Diabetologia 41: 629-633). However, also an intra-islet location or an origin in the bone marrow has been suggested for precursor cells of adult beta-cells (Zulewski et al., 2001, Diabetes 50: 521-533; Ianus at al., 2003, J Clin Invest. 111: 843-850). Pancreatic islet growth is dynamic and responds to changes in insulin demand, for example during pregnancy or due to changing body weight during childhood. In adults, there is a good correlation between body mass and islet mass (Yoon et al., 2003, J Clin Endocrinol Metab. 88: 2300-2308).

Pancreatic beta-cells secrete insulin in response to blood glucose levels. Insulin amongst other hormones plays a key role in the regulation of the fuel metabolism. Insulin leads to the storage of glycogen and triglycerides and to the synthesis of proteins. The entry of glucose into muscles and adipose cells is stimulated by insulin. In patients who suffer from diabetes mellitus type I or LADA (latent autoimmune diabetes in adults (Pozzilli & Di Mario, 2001, Diabetes Care. 8:1460-67) beta-cells are being destroyed due to autoimmune attack. The amount of insulin produced by the remaining pancreatic islet cells is too low, resulting in elevated blood glucose levels (hyperglycemia). In diabetes type II liver and muscle cells loose their ability to respond to normal blood insulin levels (insulin resistance). High blood glucose levels (and also high blood lipid levels) in turn lead to an impairment of beta-cell function and to an increase in beta-cell apoptosis. It is interesting to note that the rate of beta-cell neogenesis does not appear to change in type II diabetics (Butler et al., 2003 supra), thus causing a reduction in total beta-cell mass over time. Eventually the application of exogenous insulin becomes necessary in type II diabetics.

Improving metabolic parameters such as blood sugar and blood lipid levels (e.g. through dietary changes, exercise, medication or combinations thereof) before beta-cell mass has fallen below a critical threshold leads to a relatively rapid restoration of beta-cell function. However, after such a treatment the pancreatic endocrine function would remain impaired due to the only slightly increased regeneration rate.

In type I diabetics, where beta-cells are being destroyed by autoimmune attack, treatments have been devised which modulate the immune system and may be able to stop or strongly reduce islet destruction (Raz et al., 2001, Lancet 3513: 1749-1753; Chatenoud et al., 2003, Nat Rev Immunol. 3: 123-132; Homann et al., Immunity. 2002, 3:403-15). However, due to the relatively slow regeneration of human beta-cells such treatments can only be successful if they are combined with agents that can stimulate beta-cell regeneration.

Diabetes is a very disabling disease, because today's common anti-diabetic drugs do not control blood sugar levels well enough to completely prevent the occurrence of high and low blood sugar levels. Out of range blood sugar levels are toxic and cause long-term complications like for example renopathy, retinopathy, neuropathy and peripheral vascular disease. There is also a host of related conditions, such as obesity, hypertension, heart disease and hyperlipidemia, for which persons with diabetes are substantially at risk.

Apart from the impaired quality of life for the patients, the treatment of diabetes and its long term complications presents an enormous financial burden to our healthcare systems with rising tendency. Thus, for the treatment of, type I and type II diabetes as well as for latent autoimmune diabetes in adults (LADA) there is a strong need in the art to identify factors that induce regeneration of pancreatic insulin producing beta-cells. These factors could restore normal function of the endocrine pancreas once its function is impaired or event could prevent the development or progression of diabetes type I, diabetes type II, or LADA.

In this invention, we disclose a novel and so far unknown use for the neurotrophic factor neurturin to stimulate the formation or regeneration of insulin producing beta-cells and thus, a use in the treatment and prevention of diabetes.

Neurotrophic factors are growth factors that regulate the survival and maintain the phenotypic differentiation of certain nerve and/or glial cell populations (Varon at al., 1978, Ann. Rev. Neurosience 1: 327-361; Thoenen at al., Science, 229:238-242, 1985). Nerve growth factor (NGF) was the first neurotrophic factor to be identified and characterized (Levi-Montalcini at al., 1951, J. Exp. Zool. 116:321). The second member of this family to be discovered was brain-derived neurotrophic factor (Leibrock at al., 1989, Nature 341:149-152).

Glial-derived neurotrophic factor (GDNF)® a neurotrophic factor structurally unrelated to NGF—was discovered during a search for factors crucial to the survival of midbrain dopaminergic neurons, which degenerate in Parkinson's disease (Lin at al., 1993, Science 260:1130-2). Sequence analysis revealed it to be a distant member of the superfamily of transforming growth factor 8 (TGF-beta) factors.

Another neurotrophic factor that is structurally closely related to GDNF and unrelated to NGF is neurturin (Kotzbauer et al., 1996, Nature 384: 467-470). Neurturin, GDNF and two other related factors (artemin and persephin) define a family of neurotrophic factors referred to as TGF-beta-related neurotrophins. These neurotrophic factors promote the survival of various neurons including peripheral autonomic and sensory neurons as well as central motor and dopamine neurons, and have been proposed as therapeutic agents for neurodegenerative diseases (see review by Takahashi, 2001, Cytokine Growth Factor Rev 12(4):361-73; see also, for example, U.S. Pat. No. 6,090,778 and EP1005358B1, the disclosures of which are hereby incorporated by reference). TGF-beta-related neurotrophins signal through a unique two-receptor complex consisting of a glycosylphosphatidylinositol-linked cell surface molecule, the GDNF family receptor alpha (GFRalpha) and receptor protein tyrosine kinase Ret.

Apart from the described functions in neuronal tissue GDNF/RET signalling is crucial for the differentiation of certain non-neuronal tissues. For example, GFRalpha1 and the Ret are both necessary receptor components for ureteric bud outgrowth and subsequent branching in the developing kidney (Cacalano at al., 1998, Neuron 21:53-62; Tang at al., 1998, J. Cell Biol. 142 (5):1337-45). Ret, GFRalpha-1 (the GDNF receptor), and GFRalpha-2 (the Neurturin receptor) are expressed by testicular germ cells, while GDNF and Neurturin are expressed by Sertoli cells. Both GDNF and Neurturin stimulate DNA synthesis in spermatogonia. Furthermore, GFRalpha, GFRalpha ligands and co-receptors are expressed in germ cell tumors and thus may act as paracrine factors in spermatogenesis (Viglietto at al., 2000, Int J Oncol. 16(4):689-94).

Only recently, it was shown that the biology of GDNF signalling is much more complex than originally assumed. GDNF family ligands also signal through the neural cell adhesion molecule NCAM. In cells lacking Ret, GDNF binds with high affinity to the NCAM and GFRalpha1 complex (see review by Sariola & Saarma, 2003, J Cell Sol. 116(Pt 19): 3855-62). Signalling via the c-met receptor kinases has also been demonstrated (see Popsueva et al., 2003, J Cell Biol. 161(1):119-29).

Although it has been discussed in the prior art that GDNF/RET signalling is crucial for the differentiation of neuronal and certain non-neuronal tissues, it has not been disclosed that a member of family of TGF-beta-related neurotrophins is involved in the regeneration of pancreatic tissue. We found surprisingly, that neurturin stimulates the formation or regeneration of insulin producing pancreatic beta-cells which play an essential role in diabetes. Thus, in this invention, we disclose the use of neurturin in the treatment and prevention of diabetes.

SUMMARY OF THE INVENTION

The present invention relates to new methods for stimulating and/or inducing the differentiation of progenitor cells, e.g. stem cells into insulin-producing cells or for promoting the protection, survival and/or regeneration of insulin producing cells using a neurturin product and/or a modulator/effector thereof that influences, particularly increases the expression level or function of a neurturin protein product.

Thus, the present invention provides methods for treating patients suffering is from a disease caused by, associated with, and/or accompanied by functionally impaired and/or reduced numbers of pancreatic islet cells, particularly insulin producing beta-cells, by administering a therapeutically effective amount of a neurturin product or a compound that influences the neurturin expression level or function. Functional impairment or loss of pancreatic islet cells may be due to e.g. autoimmune attack such as in diabetes type I or LADA, and/or due to cell degeneration such as in progressed diabetes type II. The methods of the present invention may also be used to treat patients at risk to develop degeneration of insulin producing beta-cells to prevent the start or progress of such process.

The neurturin product or the effector/modulator thereof may be administered e.g. as a pharmaceutical composition, via implantation of neurturin product expressing cells, and/or via gene therapy.

Further, the invention relates to cell preparations comprising neurturin-treated insulin producing cells or neurturin expressing cells.

Numerous additional aspects and advantages of the invention will become apparent to those skilled in the art upon consideration of the following description of the Figures and detailed description of the invention which describes presently preferred embodiments thereof.

Mouse embryonic stem (ES) cells were differentiated to insulin producing cells as described previously (patent application PCT/EP02/04362, published as WO 02/086107, which is incorporated herein by reference). In differentiated cells, the abundance of insulin mRNA (FIGS. 1A and 1B) and of beta-cell glucose transporter Glut2 mRNA (FIGS. 1C and 1D) was determined using quantitative RT-PCR in two independent examples. Levels were normalized using 18S RNA as control and a cycle number of 36 as reference. The numbers on the vertical line refer to the abundance of the indicated transcripts relative to an abundance for which 36 cycles are necessary for detection, 'wt ES' refers to unmodified mouse R1 embryonic stem (ES) cells; 'Pax4 ES' refers to R1 mouse embryonic stem (ES) cells stably transfected with a CMV-Pax4 expression construct; 'insulin expression rel. to delta Ct36' refers to expression of insulin; 'Glut2 expression rel. to delta Ct36' refers to expression of beta-cell glucose transporter; 'ES' refers to mouse embryonic stem cells, as described in Example 1; 'control' refers to the differentiation protocol as described in Example 2, without any addition of neurturin; 'EB+NTN' refers to the differentiation protocol as described in Example 3, with the addition of neurturin to embryoid bodies).

Figure 2:
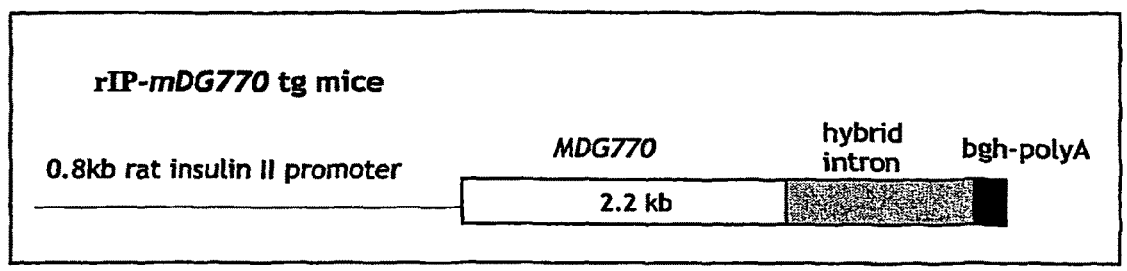

FIG. 2 shows the structure of the mouse mDG770 transgenic construct, Shown is the HP promoter (0.8 kb rat insulin II promoter) as a thin line, the mouse DG770 cDNA (mDG77U) as white box, the hybrid-intron structure (hybrid-intron) as grey box and the polyadenylation signal (bgh-polyA) as black box.

Figure 3:
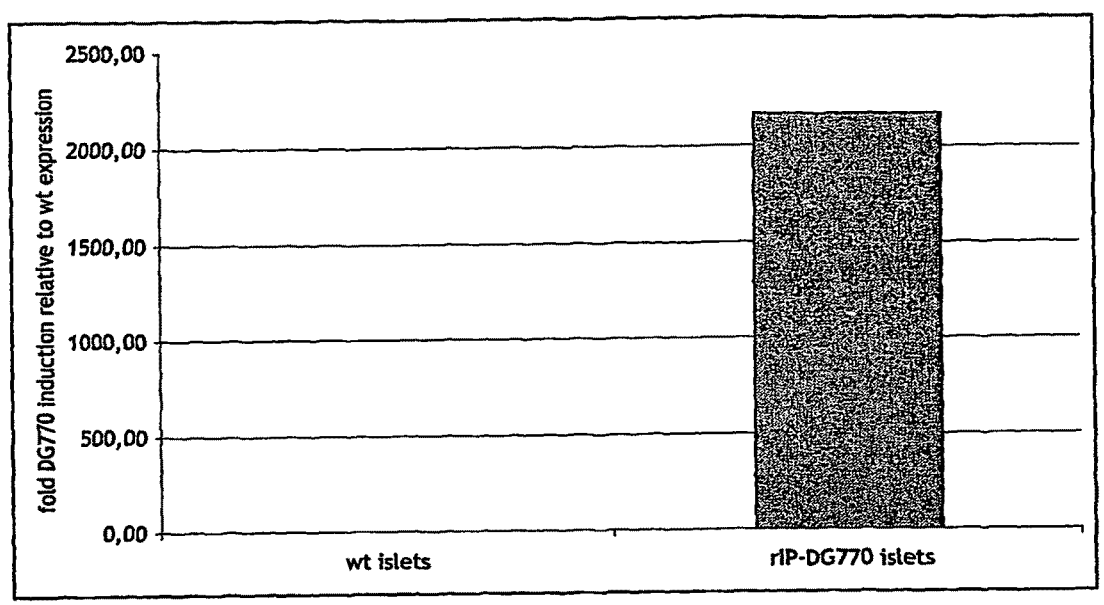

FIG. 3 shows pancreatic islets of mDG770 transgenic mice with ectopic mDG770 expression. Taqman expression analysis on islet cDNA isolated from two wild type and two transgenic fillet mates using a mDG770 specific primer/probe pair. The data are presented as fold mDG770 induction relative to wild type mDG770 expression in islets.

Figure 4:
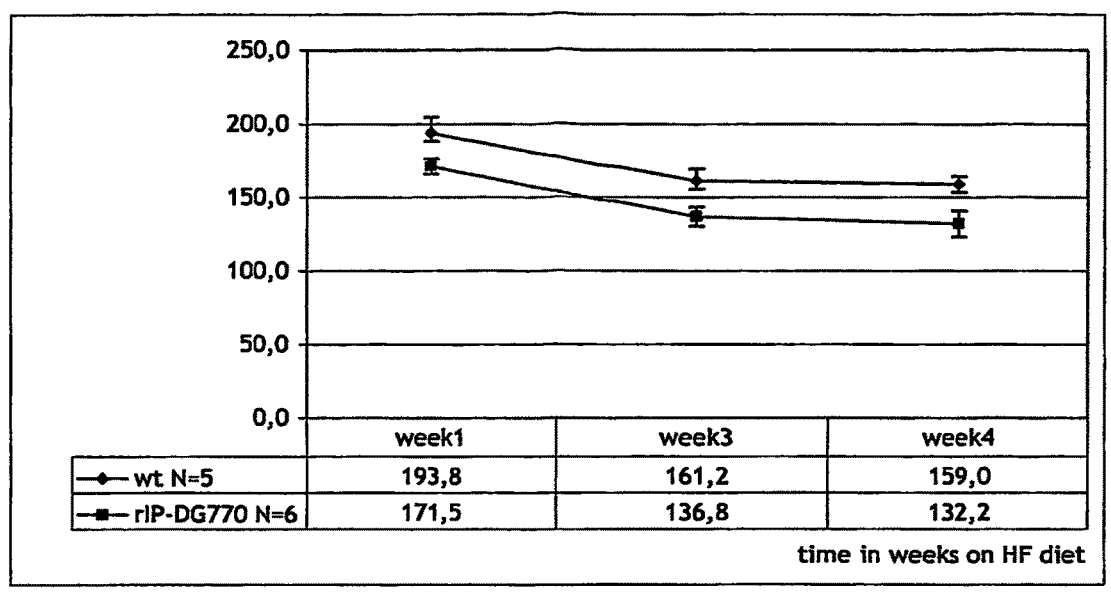

FIG. 4 shows random fed blood glucose levels of DG770 transgenic mice (rIP-rnDG770) compared to wild type mice (wt) on high fat (HF) diet. Shown are blood glucose levels from random fed male wild type mice (♦, N=5) and rIP-mDG770 transgenic mice (■, N=6). The data are expressed as mean blood glucose +/– standard deviation. The blood glucose levels are significantly lower in DG770 transgenic mice; meaning that higher expression of DG770 in pancreatic islets of mammals will lower the blood glucose level.

DETAILED DESCRIPTION OF THE INVENTION

Before the present invention is described, it is understood that all technical and scientific terms used herein have the same meanings as commonly understood by one of ordinary skill in the art to which this invention belongs.

In the present invention the term "beta-cell regeneration" refers to an at least partial restoration of normal beta-cell function by increasing the number of functional insulin secreting beta-cells and/or by restoring normal function in functionally impaired beta-cells.

As used herein, the term "neurturin product" includes neurturin protein products such as purified natural or synthetic neurturin and variants thereof. Variants include insertion, substitution and deletion variants and chemically modified derivatives. Variants also include recombinant proteins, for example but not limited to hybrids of neurturin and other TGF-beta proteins (preferably from the GDNF-family). Also included are proteins or peptides substantially homologous to the human neurturin precursor protein having the amino acid sequence published as GenBank Accession Number NP_004549 (SEQ ID NO: 7 and the corresponding coding nucleotide sequence from GenBank Accession Number U78110 disclosed as SEQ ID NO: 6). The term "neurturin product" also includes polynucleotides (e.g. mRNA/DNA) encoding the above described neurturin protein product. The term "neurturin product" also includes neurturin homodimers or heterodimers of a neurturin protein product and another protein, wherein the other protein preferably belongs to the GDNF-family.

The term "biologically active" as used herein means that the neurturin product induces and/or stimulates the differentiation of insulin producing cells from progenitor, e.g. stem cells and/or promotes the protection, survival, or regeneration of insulin producing cells, e.g. beta-cells. The biological activity of neurturin products may be determined as described in the Examples of the present application.

The term "substantially homologous" as used herein means having a degree of homology to the biologically active human neurturin product resulting from the cleavage of the neurturin precursor having the amino acid sequence published as GenBank Accession Number NP_004549 (SEQ ID NO: 7 and the corresponding coding nucleotide sequence from GenBank Accession Number U78110 disclosed as SEQ ID NO: 6) or to the human neurturin precursor itself, that is preferably in excess of 70%, most preferably in excess of 80%, and even more preferably in excess of 90% or 95%. The degree of homology between the mouse and the human protein is about 91%, and it is contemplated that preferred mammalian neurturin proteins will have a similarly high degree of homology. Also included are proteins which are hybrids between neurturin and another TGFbeta-protein, preferably another member of the GDNF-family which retain the stimulatory effect on islet cell formation found in Neurturin. The percentage of homology or identity between a neurturin product and the human neurturin protein or a precursor or a nucleic acid coding therefor may be determined according to standard procedures, e.g. by using the BLAST algorithm. Preferably, the percentage of homology or identity is calculated as the percentage of nucleotide or amino acid residues found in the smaller of the two sequences that align with identical nucleotides or amino acid residues in the sequence being compared, when four gaps in a length of 100 nucleotides or amino acids may be introduced to assist in that alignment. Also included as substantially homologous is any neurturin protein product which may be isolated by virtue of cross-reactivity with antibodies to the neurturin protein product or whose genes may be isolated through hybridization with the gene or with segments of the gene encoding the neurturin protein product.

In connection with the present invention, the term "progenitor cells" relates to undifferentiated cells capable of being differentiated into insulin producing cells. The term particularly includes stem cells, i.e. undifferentiated or immature embryonic, adult, or somatic cells that can give rise to various specialized cell types. The term "stem cells" can include embryonic stem cells (ES) and primordial germ cells (EG) cells of mammalian, e.g. human or animal origin. Isolation and culture of such cells is well known to those skilled in the art (see, for example, Thomson et al., 1998, Science 282: 1145-1147; Shamblott at al., 1998, Proc. Natl. Acad. Sci. USA 95:13726-13731; U.S. Pat. No. 6,090,622; U.S. Pat. No. 5,914,268; WO 0027995; Notarianni at al., 1990, J. Reprod. Fart. 41:51-56; Vassilieva at al., 2000, Exp. Cell. Res. 258: 361-373). Adult or somatic stem cells have been identified in numerous different tissues such as intestine, muscle, bone marrow, liver, and brain. WO 03/023018 describes a novel method for isolating, culturing, and differentiating intestinal stem cells for therapeutic use. In the pancreas, several indications suggest that stem cells are also present within the adult tissue (Gu & Sarvetnick, 1993, Development 118:33-46; Bouwens, 1998, Microsc Res Tech 43:332-336; Bonner-Weir, 2000, J. Mol. Endocr. 24:297-302).

Embryonic stem cells can be isolated from the inner cell mass of pre-implantation embryos (ES cells) or from the primordial germ cells found in the genital ridges of post-implanted embryos (EG cells). When grown in special culture conditions such as spinner culture or hanging drops, both ES and EG cells aggregate to form embryoid bodies (EB). EBs are composed of various cell types similar to those present during embryogenesis. When cultured in appropriate media, EB can be used to generate in vitro differentiated phenotypes, such as extraembryonic endoderm, hematopoietic cells, neurons, cardiomyocytes, skeletal muscle cells, and vascular cells. We have previously described a method that allows EB to efficiently differentiate into insulin-producing cells (as described in patent application PCT/EP02/04362, published as WO 02/086107 and by Blyszczuk at al., 2003, Proc Natl Aced Sci USA. 100(3):998-1003, which are incorporated herein by reference).

The term 'cultivation medium' means a suitable medium capable of supporting growth and differentiation of stem cells. The term 'differentiation medium' means a suitable medium for inducing the differentiation of stem cells into insulin-producing cells. The term 'terminal differentiation medium' means a suitable medium for terminal differentiation of insulin-producing cells. Examples of preferred media are described in WO/023018, which are herein incorporated by reference.

In this invention, we disclose a novel and so far unknown use for the neurotrophic factor neurturin to stimulate and/or induce the formation or regeneration of insulin producing cells and thus, a use in the treatment and prevention of diseases going along with (e.g. caused by, associated with or accompanied by) impaired beta cell function, for example but not limited to diabetes mellitus. More particularly, the diseases are diabetes type I, diabetes type II or LADA.

The present invention is based on the surprising finding that neurturin stimulates the differentiation of insulin producing cells from stem cells in vitro. Thus, a therapeutically effective amount of neurturin product may be administered to promote the regeneration of pancreatic beta-cells or to promote the formation of insulin-producing cells from stem cells or progenitor cells in vitro or in vivo. The present invention further relates to applications in the medical field that directly arise from the method of the invention. Additionally, the present invention relates to applications for the identification and characterization of compounds with therapeutic medical effects or toxicological effects that directly arise from the method of the invention.

According to this invention the neurturin product may be administered
i) as a pharmaceutical composition e.g. enterally, parenterally or topically, preferably directly to the pancreas,
ii) via implantation of neurturin protein product expressing cells, and/or
iii) via gene therapy
as described in more detail below.

Further, the neurturin expression level in a patient might be influenced by a neurturin modulator/effector administered
i) as a pharmaceutical composition e.g. enterally, parenterally or topically, preferably directly to the pancreas,
ii) via cell based therapy, and/or
iii) via gene therapy
as described in more detail below.

The neurturin product or the neurturin modulator/effector, i.e. a pharmaceutically active substance influencing, particularly increasing the neurturin expression level or function may be administered in the above described manner alone or in combination with another pharmaceutical composition useful to treat beta-cell degeneration, for example hormones, growth factors or immune modulating agents.

A neurturin product or a modulator/effector thereof may be administered in patients suffering from a disease going along with impaired beta-cell function, for example but not limited to diabetes type I, LADA, or progressed diabetes type II. It is further contemplated that a neurturin product or the modulator/effector thereof may be administered preventively to patients at risk to develop beta-cell degeneration, like for example but not limited to patients suffering from diabetes type II or LADA in early stages. A variety of pharmaceutical formulations and different delivery techniques are described in further detail below.

The present invention also relates to methods for differentiating progenitor cells into insulin-producing cells in vitro comprising
(a) activating one or more pancreatic genes in a progenitor, e.g. stem cell (optional step, particularly if embryonic stem cells are used)
(b) aggregating said cells to form embryoid bodies (optional step, particularly if embryonic stem cells are used)
(c) cultivating embryoid bodies or cultivating adult stem cells (e.g., duct cells) in specific differentiation media containing a neurturin protein product and/or a modulator/effector thereof under conditions wherein beta-cell differentiation is significantly enhanced, and
(d) identifying and selecting insulin-producing cells.

Activation of pancreatic genes may comprise transfection of a cell with pancreatic gene operatively linked to an expression control sequence, e.g. is on a suitable transfection vector, as described in WO 03/023018, which is herein incorporated by reference. Examples of preferred pancreatic genes are Pdx1, Pax4, Pax6, neurogenin 3 (ngn3), Nkx 6.1, Nkx 6.2, Nkx 2.2, HB 9, BETA2/Neuro D, Isl 1, HNF1-alpha, HNF1-beta and HNF3 of human or animal origin. Each gene can be used individually or in combination with at least one other gene, Pax4 is especially preferred.

Neurturin products, e.g. neurturin protein or nucleic acid products, are preferably produced via recombinant techniques because such methods are capable of achieving high amounts of protein at a great purity, but are not limited to products expressed in bacterial, plant, mammalian, or insect cell systems.

Neurturin Protein Product

Recombinant neurturin protein product forms include glycosylated and non-glycosylated forms of the protein. In general, recombinant techniques involve isolating the genes encoding for neurturin protein product, cloning the gene in suitable vectors and/or cell types, modifying the gene if necessary to encode a desired variant, and expressing the gene in order to produce the neurturin protein product.

Alternatively, a nucleotide sequence encoding the desired neurturin product may be chemically synthesized. It is contemplated that a neurturin product may be expressed using nucleotide sequences that vary in codon usage due to the degeneration of the genetic code or allelic variations or alterations made to facilitate production of the protein product by the selected cell.

Kotzbauer et al., Nature 384:467470, describe the identification of a mouse cDNA and amino acid sequence and a human cDNA and amino acid sequence for neurturin protein. The neurturin products according to this invention may be isolated or generated by a variety of means. Exemplary methods for producing neurturin products useful are described in patent application WO 97/08196, the disclosures of which are hereby incorporated is by reference. Also described are a variety of vectors, host cells, and culture growth conditions for the expression of neurturin protein, as well as methods to synthesize variants of neurturin protein product. Additional vectors suitable for the expression of neurturin protein product in *E. coli* are disclosed in Patent No. EP 0 423 980, the disclosure of which is hereby incorporated by reference.

The molecular weight of purified neurturin indicates that in its biologically active form the protein is a disulfide-bonded dimer. The material isolated after expression in a bacterial system is essentially biologically inactive, and exists as a monomer. Refolding is necessary to produce the biologically active disulfide-bonded dimer. Processes suitable for the refolding and maturation of the neurturin expressed in bacterial systems are substantially similar to those described in WO93/06116. Standard in vitro assays for the determination of neurturin activity are also substantially similar to those determining GDNF activity as described in WO93/06116 and in U.S. application Ser. No. 08/535,681, and are hereby incorporated by reference.

Neurturin product variants are prepared by introducing appropriate nucleotide changes into the DNA encoding the polypeptide or by in vitro chemical synthesis of the desired polypeptide. It will be appreciated by those skilled in the art that many combinations of deletions, insertions, and substitutions can be made resulting in a protein product variant presenting neurturin biological activity.

Mutagenesis techniques for the replacement, insertion or deletion of one or more selected amino acid residues are well known to one skilled in the art (e.g., U.S. Pat. No. 4,518,584, the disclosure of which is hereby incorporated by reference.)

Neurturin substitution variants have at least one amino acid residue of the human or mouse neurturin amino acid sequence removed and a different residue inserted in its place. Such substitution variants include allelic variants, which are characterized by naturally occurring nucleotide sequence changes in the species population that may or may not result in an amino acid change.

Chemically modified derivatives of neurturin protein products also may be prepared by one of skill in the art given the disclosures herein. The chemical moieties most suitable for derivatization include water soluble polymers. A water soluble polymer is desirable because the protein to which it is attached does not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically, and if so, the desired dosage, circulation time, resistance to proteolysis, and other considerations. A particularly preferred water-soluble polymer for use herein is polyethylene glycol. Attachment at residues important for receptor binding should be avoided if receptor binding is desired. One may specifically desire an N-terminal chemically modified protein.

The present invention contemplates use of derivatives which are prokaryote-expressed neurturin, or variants thereof, linked to at least one polyethylene glycol molecule, as well as use of neurturin, or variants thereof, attached to one or more polyethylene glycol molecules via an acyl or alkyl linkage. Pegylation may be carried out by any of the pegylation reactions known in the art. See, for example: Focus on Growth Factors, 3 (2):4-10, 1992; EP 0 154 316, the disclosure of which is hereby incorporated by reference; EP 0 401 384; and the other publications cited herein that relate to pegylation.

The present invention also discloses use of derivatives which are prokaryote-expressed neurturin, or variants thereof, linked to at least one hydrophobic residue, for example fatty acid molecule, as well as use of neurturin, or variants thereof, attached to one or more hydrophobic residues. For example, patent application published as WO 03/010185, which is hereby incorporated by reference, describes a method for producing acylated polypeptides in transformed host cells by expressing a precursor molecule of the desired polypeptide which are then to be acylated in a subsequent in vitro step.

Polynucleotides Encoding Neurturin Protein Product

The present invention further provides polynucleotides that encode neurturin protein products, whether recombinantly produced or naturally occurring.

A nucleic acid sequence encoding a neurturin protein product, can readily be obtained in a variety of ways, including, without limitation, chemical synthesis, cDNA or genomic library screening, expression library screening, and/or PCR amplification of cDNA. These methods and others useful for isolating such nucleic acid sequences are set forth, for example, by Sambrook et al. (Molecular Cloning: A Laboratory Manual, Cold Spring Harbor Laboratory Press, Cold Spring Harbor, N.Y., 1989), by Ausubel et al, eds (Current Protocols in Molecular Biology, Current Protocols Press, 1994), and by Berger and Kimmel (Methods in Enzymology: Guide to Molecular Cloning Techniques, vol. 152, Academic Press, Inc., San Diego, Calif., 1987). Chemical synthesis of a nucleic acid sequence which encodes a neurturin protein product can also be accomplished using methods well known in the art, such as those set forth by Engels et al. (Angew. Chem. Intl. Ed., 28:716-734, 3 0 1989).

Included within the scope of this invention are neurturin product polynucleotides with the native signal sequence and other pre-pro sequences as well as polynucleotides wherein the native signal sequence is deleted and replaced with a heterologous signal sequence. The heterologous signal sequence selected should be one that is recognized and processed, i.e., cleaved by a signal peptidase, by the host cell. For prokaryotic host cells that do not recognize and process the native neurturin signal sequence, the signal sequence is substituted by a prokaryotic signal sequence selected, for example, from the group of the alkaline phosphatase, penicillinase, or heat-stable enterotoxin 11 leaders. For yeast secretion, the native neurturin signal sequence may be substituted by the yeast invertase, alpha factor, or acid phosphatase leaders. In mammalian cell expression the native signal sequence is satisfactory, although other mammalian signal sequences may be suitable.

Expression and cloning vectors generally include a nucleic acid sequence that enables the vector to replicate in one or more selected host cells.

Neurturin Product Pharmaceutical Compositions

Neurturin product pharmaceutical compositions typically include a therapeutically effective amount of a neurturin product in admixture with one or more pharmaceutically and physiologically acceptable formulation. In addition to the active ingredients, neurturin product pharmaceutical compositions may contain suitable pharmaceutically acceptable carriers comprising excipients and auxiliaries, which facilitate processing of the active compounds into preparations, which can be used pharmaceutically. Further details on techniques for formulation and administration may be found in the latest edition of Remington's Pharmaceutical Sciences (Maack Publishing Co., Easton, Pa.), the disclosure of which is hereby incorporated by reference.

Once the therapeutic composition has been formulated, it may be stored in sterile vials as a solution, suspension, gel, emulsion, solid, or dehydrated or lyophilized powder. Such formulations may be stored either in a ready to use form or in a form, e.g., lyophilized, requiring reconstitution prior to administration. The optimal pharmaceutical formulations will be determined by one skilled in the art depending upon considerations such as the route of administration and desired dosage. Such formulations may influence the physical state, stability, rate of in vivo release, and rate of in vivo clearance of the present neurturin proteins, variants and derivatives. Other effective administration forms, such as slow-release formulations, inhalant mists, or orally active formulations are also envisioned.

For example, in a sustained release formulation, the neurturin product may be bound to or incorporated into particulate preparations of polymeric compounds (such as polylactic acid, polyglycolic acid, etc.) or liposomes.

Administration/Delivery Neurturin Product

The neurturin product may be administered by any suitable means, preferably enterally or parenterally or topically directly to the pancreas, as known to those skilled in the art. The specific dose may be calculated according to considerations of body weight, body surface area or organ size. Further refinement of the calculations necessary to determine the appropriate dosage for treatment involving each of the above mentioned formulations is routinely made by those of ordinary skill in the art and is within the ambit of tasks routinely performed. Appropriate dosages may be ascertained through use of the established assays for determining dosages utilized in conjunction with appropriate dose-response data. The final dosage regimen involved in a method for treating the above described conditions will be determined by the attending physician, considering various factors which modify the action of drugs, e.g., the age, condition, body weight, sex and diet of the patient, the severity of any infection, time of administration and other clinical factors. As studies are conducted, further information will emerge regarding the appropriate dosage levels for the treatment of various diseases and conditions.

It is envisioned that the continuous administration or sustained delivery of a neurturin product may be advantageous for a given treatment. While continuous administration may be accomplished via a mechanical means, such as with an infusion pump, it is contemplated that other modes of continuous or near continuous administration may be practiced. For example, chemical derivatization or encapsulation may result in sustained release forms of the protein having the effect of continuous presence, in predictable amounts, based on a determined dosage regimen. Thus, neurturin protein products include proteins derivatized or otherwise formulated to effectuate such continuous administration.

Neurturin product cell therapy, i.e. pancreatic implantation of cells producing neurturin protein product, is also contemplated. This embodiment would involve implanting cells capable of synthesizing and secreting a biologically active form of neurturin protein product into patients. Such neurturin protein product-producing cells may be cells that are natural producers of neurturin protein product or may be cells that are modified to express the protein. Such modified cells include recombinant cells whose ability to produce a neurturin protein product has been augmented by transformation with a gene encoding the desired neurturin protein product in a vector suitable for promoting its expression and secretion. In order to minimize a potential immunological reaction in patients being administered neurturin protein product of a foreign species, it is preferred that the cells producing neurturin protein product be of human origin and produce human neurturin protein product. Likewise, it is preferred that the recombinant cells producing neurturin protein product be transformed with an expression vector containing a gene encoding a human neurturin protein product. Implanted cells may be encapsulated to avoid infiltration of surrounding tissue. Human or nonhuman animal cells may be implanted in patients in biocompatible, semipermeable polymeric enclosures or membranes that allow release of neurturin protein product, but that prevent destruction of the cells by the patient's immune system or by other detrimental factors from the surrounding tissue.

Alternatively, neurturin protein product secreting cells may be introduced into a patient in need intraportally via a percutaneous transhepatic approach using local anaesthesia. Between 3000 and 100 000 equivalent differentiated insulin-producing cells per kilogram body weight are preferably administered. Such surgical techniques are well known in the art and can be applied without any undue experimentation, see Pyzdrowski et al, 1992, New England J. Medicine 327: 220-226; Hering et al., Transplantation Proc. 26:570-571, 1993; Shapiro et al., New England J. Medicine 343:230-238, 2000.

In a further preferred embodiment, neurturin protein product can be delivered directly to progenitor, e.g. stem cells in order to stimulate the differentiation of insulin producing cells. For example, protein delivery can be achieved by polycationic liposomes (Sells et al. (1995) Biotechniques 19:72-76), Tat-mediated protein transduction (Fawell et al. (1993) Proc. Natl. Acad. Sci. USA 91:664-668) and by fusing a protein to the cell permeable motif derived from the PreS2-domain of the hepatitis-B virus (Oess and Hildt (2000) Gene Ther. 7150-758). Preparation, production and purification of such proteins from bacteria, yeast or eukaryotic cells are well known by persons skilled in the art. In this embodiment of the invention, neurturin may be added preferably at concentrations between ng/ml and 500 ng/ml, more preferably between 10 and 100 ng/ml, e.g. at about 50 ng/ml.

Further, the invention relates to a cell preparation comprising differentiated progenitor cells, e.g. stem cells exhibiting insulin production, particularly an insulin-producing cell line obtainable by the method described above. The insulin-producing cells may exhibit a stable or a transient expression of at least one pancreatic gene involved in beta-cell differentiation. The cells are preferably human cells that are derived from human stem cells. For therapeutic applications the production of autologous human cells from adult stem cells of a patient is especially preferred. However, the insulin producing cells may also be derived from non-autologous cells. If necessary, undesired immune reactions may be avoided by encapsulation, immunosuppression and/or modulation or due to non-immunogenic properties of the cells.

The insulin producing cells of the invention preferably exhibit characteristics that closely resemble naturally occurring beta-cells. Further, the cells of the invention preferably are capable of a quick response to glucose. After addition of 27.7 mM glucose, the insulin production is enhanced by a factor of at least 2, preferably by a factor of at least 3. Further, the cells of the invention are capable of normalizing blood glucose levels after transplantation into mice.

The invention further encompasses functional pancreatic cells obtainable or obtained by the method according to the invention. The cells are preferably of mammalian, e.g. human origin. Preferably, said cells are pancreatic beta-cells, e.g. mature pancreatic beta-cells or stem cells differentiated into pancreatic beta-cells. Such pancreatic beta cells preferably secrete insulin in response to glucose. Moreover, the present invention provides functional pancreatic cell that express glucagon in response to glucose. A preparation comprising the cells of the invention may additionally contain cells with properties of other endocrine cell types such as alpha-cells, delta-cells and/or PP-cells. These cells are preferably human cells.

The cell preparation of the invention is preferably a pharmaceutical composition comprising the cells together with pharmacologically acceptable carriers, diluents and/or adjuvants. The pharmaceutical composition is preferably used for the treatment or prevention of pancreatic diseases, e.g. diabetes.

According to the present invention, the functional insulin producing cells treated with neurturin may be transplanted preferably intrahepatic, directly into the pancreas of an individual in need, or by other methods. Alternatively, such cells may be enclosed into implantable capsules that can be introduced into the body of an individual, at any location, more preferably in the vicinity of the pancreas, or the bladder, or the liver, or under the skin. Methods of introducing cells into individuals are well known to those of skill in the art and include, but are not limited to, injection, intravenous or parenteral administration. Single, multiple, continuous or intermittent administration can be effected. The cells can be introduced into any of several different sites, including but not limited to the pancreas, the abdominal cavity, the kidney, the liver, the celiac artery, the portal vein or the spleen. The cells may also be deposited in the pancreas of the individual.

The methodology for the membrane encapsulation of living cells is familiar to those of ordinary skill in the art, and the preparation of the encapsulated cells and their implantation in patients may be accomplished without undue experimentation. See, e.g., U.S. Pat. Nos. 4,892,538, 5,011,472, and 5,106.627, each of which is specifically incorporated herein by reference. A system for encapsulating living cells is described in PCT Application WO 91/10425 of Aebischer et al., specifically incorporated herein by reference. See also, PCP Application WO 91/10470 of Aebischer et al., Winn et al., Exper. Neurol., 1 13:322-329, 1991, Aebischer et al., Exper. Neurol., 11 1:269-275, 1991; Tresco et al., ASAIO, 38:17-23, 1992, each of which is specifically incorporated herein by reference. Techniques for formulating a variety of other sustained- or controlled-delivery means, such as liposome carriers, bio-erodible particles or beads and depot injections, are also known to those skilled in the art.

In another embodiment gene therapy ex vivo is envisioned, i.e. the patient's own cells may be transformed ex vivo to produce a neurturin protein product or a protein stimulating neurturin expression and would be directly reimplanted. For example, cells retrieved from the patient may be cultured and transformed with an appropriate vector. After an optional propagation/expansion phase, the cells can be transplanted back into the same patient's body, particularly the pancreas, where they would produce and release the desired neurturin protein product. Delivery by transfection and by liposome injections may be achieved using methods, which are well known in the art. Any of the therapeutic methods described above may be applied to any suitable subject including, for example, mammals such as dogs, cats, cows, horses, rabbits, monkeys, and most preferably, humans.

Neurturin product gene therapy in vivo is also envisioned, by introducing the gene coding for a neurturin protein product into targeted pancreas cells via local injection of a nucleic acid construct or other appropriate delivery methods (Hefti, J. Neurobiol., 25:1418-1435, 1994). For example, a nucleic acid sequence encoding a neurturin protein product may be contained in an adeno-associated virus vector or adenovirus vector for delivery to the pancreas cells. Alternative viral vectors include, but are not limited to, retrovirus, herpes simplex virus and papilloma virus vectors. Physical transfer, either in vivo or ex vivo as appropriate, may also be achieved by liposome-mediated transfer, direct injection (naked DNA), receptor-mediated transfer (ligand-DNA complex), electroporation, calcium phosphate precipitation or microparticle bombardment (gene gun).

Immunosuppressive drugs, such as cyclosporin, can also be administered to the patient in need to reduce the host reaction versus graft. Allografts using the cells obtained by the methods of the present invention are also useful because a single healthy donor could supply enough cells to regenerate at least partial pancreas function in multiple recipients.

The neurturin nucleic acid and protein and effectors/modulators thereof may be administered either as a monotherapy or as a combination therapy with other pharmaceutical agents. For example, they may be administered together with other pharmaceutical agents suitable for the treatment or prevention of pancreatic diseases and/or obesity and/or metabolic syndrome, particularly with other pharmaceutical agents suitable for stimulating and/or inducing the differentiation of insulin producing cells from progenitor cells. Further, they may be administered together with pharmaceutical agents which have an immunosuppressive activity, e.g. antibodies, polypeptides and/or peptidic or non-peptidic low molecular weight substances. Preferred examples of immunosuppressive agents are listed in the following Table 1.

TABLE 1

Exemplary agents for immune suppression

| Names | Mechanism |
|---|---|
| 2-amino-1,3-propanediol derivatives | Used for preventing or treating chronic rejection in a patient receiving an organ or tissue allo- or xenotransplant |
| 2-amino-2[2-(4-octylphenyl)ethyl] propane-1,3-diol hydrochloride | Immunosuppression, from accelerated lymphocyte homing |
| 40-O-(2-hydroxyethyl)-rapamycin, SDZ-RAD, Everolimus | Sirolimus (rapamycin) derivative, used for acute kidney rejection; reduces rejection and graft vasculopathy following heart transplantation by inhibiting cell proliferation |
| 6-(3-dimethyl-aminopropionyl) forskolin | Immunosuppressing action useful also for treating autoimmune disease |
| 6-mercaptopurine (6-MP) | Used to treat Crohn's disease, inflammatory bowel disease and for organ transplant therapy |
| A-420983 | Lck-inhibitor |
| ABX-CBL (CBL-1) | Mouse monoclonal AB targeted against human T-cell, B cells, NK cells and monocytes, for treatment of steroid-resistant graft vs host diseases, potential use in treatment of inflammatory and autoimmune disorders |
| Alefacept (human LFA-3 IgG1 fusion protein) | Knocks out causative memory T-lymphocytes; Used to treat psoriasis, a T-cell mediated inflammatory disorder |
| Antisense ICAM-1 inhibitor (ISIS 2302), Enlimomab, BIRR1, Alicaforsen | Mouse monoclonal AB blocks white blood cell adhesion to T-cell surface molecule (ICAM-1r); treatment of kidney transplant rejection |
| Antithymocyte immunoglobulin (ATGAM) | Anti-human thymocyte, immunoglobulin; used in reversal of acute kidney transplant rejection and will likely be used off-label for transplant induction therapy |
| Azathioprine | Treatment of rheumatoid arthritis and prevention of kidney transplant rejection, and other autoimmune or inflammatory disorders such as inflammatory bowel disease |
| Baohuoside-1 | Flavonoid; inhibits lymphocyte activation; Ma et al., Transplantation 78: 831-838, (2004) |
| basiliximab | Monoclonal AB that binds to receptor sites on T-cells, preventing activation by transplanted tissue (renal transplant) |
| BMS-279700 | Lck-inhibitor |
| BTI-322 | Mouse derived monoclonal AB targeted to CD2 receptor; used for prevention of first-time kidney rejection, and treatment of resistant rejection |
| Cladribine | Antimetabolite and immunosuppressive agent that is relatively selective for lymphocytes; used to treat lymphoid malignancies, e.g., hairycell leukemia |
| CP-690550 | JAK-3 inhibitor |
| Cyclophosphamide (CTX) | Immunosuppressant for treatment of arthritis and other auto-immune disorders and cancers |
| Cyclosporine (cyclosporin A, cyclosporin) | 11 amino acid cyclic peptide; blocks helper T-cell, immunosuppressant used in organ transplant therapy and other immune diseases |
| Daclizumab, HAT (Humanized Anti-Tac), SMART anti-Tac, anti-CD25, and | Monoclonal AB inhibits binding of IL-2 to IL-2 receptor by binding to IL-2 receptor, suppresses T-cell activity against allografts (renal transplant) |

TABLE 1-continued

Exemplary agents for immune suppression

| Names | Mechanism |
|---|---|
| humanized anti-IL2-receptor | |
| Dexamethasone (Decadron, Dexone, Dexasone) | An adrenocorticoid, effective immunosuppressant in various disorders |
| DIAPEP-277 | Immunomodulatory properties |
| Dipeptide Boronic Acid (DPBA) | Proteasome inhibitor; Wu et al., Transplantation 78: 360-366, (2004) |
| Docosahexaenoic acid (DHA) | Immunosuppressant that lowers the proportion of T cells expressing CD4 or CD8, blocks antigen recognition process; Taku et al., Journal of Agricultural and Food Chemistry 48: 1047, (2000) |
| efalizumab | T-cell modulator that target T-cells through interactions with adhesion molecules on endothelial cell surface, target migration of T-cells into the skin and target activation of T-cells; Used to treat Psoriasis |
| Efomycine M | Leukocyte adhesion inhibitor, Anti-inflammatory |
| FTY720 (oral myriocin derivative) | Alters lymphocyte infiltration into grafted tissues; used for prevention of organ rejection in kidney transplants |
| Glatiramer acetate (co-polymer-1) | Synthetic peptide copolymer; decoy that mimics structure of myelin so immune cells bind Copaxone instead of myelin; for multiple sclerosis |
| Glial fibrillary acidic protein (GFAP) | Possesses immunosuppressive activities in diabetic animal models; Winer et al., Nature Medicine 9: 198, (2003) |
| Gusperimus (15-deoxyspergualin) | Intravenous immunosuppressant; suppresses production of cytotoxic T-cells, neutrophils and macrophages |
| HLA-B2702 peptide | Human peptide, blocks action of NK cells and T-cell mediated toxicities, used for prevention of first kidney allograft rejection |
| hu1124 (anti-CD11a) | Humanized monoclonal antibody; targets CD11a receptor on surface of T cells to selectively inhibit immune system rejection of transplanted organs |
| hOKT31γ(Ala-Ala) | non Fc-binding humanized anti CD3 antibody |
| Infliximab | Monoclonal AB, binds and inactivates human TNFalpha; used to treat Crohn's disease and rheumatoid arthritis |
| Interferon | Immunomodulatory properties |
| ISAtx247 | Used to treat autoimmune diseases such as rheumatoid arthritis and psoriasis |
| isotretinoin | Immunosuppressant, reduces ability of T cells to proliferate in response to immune challenge. Vergelli et al., Immunopharmacology, 31: 191, (1997) |
| L-683,742: also described as 31-desmethoxy-31-hydroxy-L-683,590 | Treatment of autoimmune diseases, infectious diseases and/or prevention of organ transplant rejections |
| Leflunomide (ARAVA) | Antiinflammatory agent |
| Medi-500 (T10B9) | Intravenous monoclonal AB that targets human T-cells; treats acute kidney rejection and graft-vs-host disease |
| Medi-507 | Intravenous humanized AB directed against CD2 T-cell; used to treat corticosteroidresistant graft vs host disease and prevention of kidney rejection |
| Methotrexate | Antimetabolite used to treat Crohn's disease, severe psoriasis, and adult rheumatoid arthritis (and as an anti-cancer drug) |
| Mitoxantrone | Antiproliferative effect on cellular immune system including T-cells, B-cells and macrophages; used to treat hormone-refractory prostate cancer, acute myelogenous leukemia and multiple sclerosis |
| mycophenolate mofetil | Proliferation of T and B lymphocytes by blocking the synthesis of purine nucleotides; used in organ transplant therapy and inflammatory bowel disease |
| OKT4A | Mouse monoclonal AB targeted against human CD4 T cell; used for prevention of kidney transplant rejection when used in combination with other immunosuppressant drugs |
| Muromonab-CD3 | Monoclonal AB that binds to receptor sites on T-cells, preventing activation by transplanted tissue |
| Prednisolone | Corticosteroid, suppresses inflammation associated with transplant rejection |
| Psora-4 | Kv1.3-blocker |
| Rifampicin | Antibiotic; has immunomodulatory properties |
| Rituximab | CD20 antibody |
| S100β | possesses immunosuppressive activities in diabetic animal models |
| Sirolimus, Rapamycin | Immunosuppressant and potent inhibitor of cytokine (e.g.IL-2)-dependent T-cell proliferation (kidney transplant) |

The combination therapy may comprise coadministration of the medicaments during the treatment period and/or separate administration of single medicaments during different time intervals in the treatment period.

Administration of a neurturin protein product and/or modulators/effectors thereof in a pharmaceutical composition to a subject in need thereof, particularly a human patient, leads to an at least partial regeneration of pancreatic cells. Preferably, these cells are insulin producing beta-cells that will contribute to the improvement of a diabetic state. With the administration of this composition e.g. on a short term or regular basis, an increase in beta-cell mass can be achieved. This effect upon the body reverses the condition of diabetes partially or completely. As the subject's blood glucose homeostasis improves, the dosage administered may be reduced in strength. In at least some cases further administration can be discontinued entirely and the subject continues to produce a normal amount of insulin without further treatment. The subject is thereby not only treated but could be cured entirely of a diabetic condition. However, even moderate improvements in beta-cell mass can lead to a reduced requirement for exogenous insulin, improved glycemic control and a subsequent reduction in diabetic complications. In another example, the compositions of the present invention will also have efficacy for treatment of patients with other pancreatic diseases such as pancreatic cancer, dysplasia, or pancreatitis, if beta-cells are to be regenerated.

In a further embodiment, the present invention allows the production of cells for the identification and/or characterisation of compounds which stimulate beta-cell differentiation, insulin secretion and/or glucose response, more particularly of compounds which increase the neurturin expression level or function. This method is particularly suitable for in vivo testing for diagnostic applications and drug development or screening. The compound of interest is added to suitable cells and the neurturin expression or function is determined. Alternatively, a compound of interest is added to a neurturin-treated cell and the effect on cell differentiation and/or insulin production is determined. Preferably, differentiated insulin-producing cells used. Insulin levels in treated cells can be determined, e.g. quantified by Enzyme Linked Immunoabsorbent Assay (ELISA) or Radio Immuno Assay (RIA). Using this method, a large number of compounds can be screened and compounds that induce neurturin expression or support the activity of neurturin leading to a beta-cell differentiation and/or an increase in insulin secretion can be identified readily.

In a high-throughput screening method, the cells are transfected with a DNA construct, e.g. a viral or non-viral vector containing a reporter gene, e.g. the lacZ gene or the GFP gene, under regulatory control of a promoter of a gene involved in beta-cell differentiation, e.g. preferably a Pax4 promoter. The transfected cells are divided into aliquots and each aliquot is contacted with a test substance, e.g. candidate 1, candidate 2, and candidate 3. The activity of the reporter gene corresponds to the capability of the test compound to induce beta-cell differentiation.

In a further embodiment (which may be combined with the high-throughput screening as described above) a medium throughput validation is carried out. Therein, the test compound is added to cells being cultivated and the neurturin expression and/or the insulin production is determined. Following an initial high throughput assay, such as the cell based assay outlined above where e.g. a Pax4 promoter is used as marker for beta-cell regeneration, the activity of candidate molecules to induce beta-cell differentiation is tested in a validation assay comprising adding said compounds to the culture media of the embryoid bodies. Differentiation into insulin-producing cells is then evaluated, e.g. by comparison to wild type and/or Pax4 expressing cells to assess the effectiveness of a compound.

EXAMPLES

A better understanding of the present invention and of its many advantages will be had from the following examples, given by way of illustration.

Example 1

Generation of ES Cells Expressing the Pax4 Gene

Mouse R1 ES cells (Nagy et al. (1993) Proc. Natl. Aced, Sci. USA. 90: 8424-8428) were electroporated with the Pax4 gene under the control of the CMV promoter and the neomycin resistance gene under the control of the phosphoglycerate kinase 1 promoter (pGK-1).

ES cells were cultured in Dulbecco's modified Eagle's medium containing 4.5 g/l glucose, $10^{-4}$ M beta-mercaptoethanol, 2 nM glutamine, 1% non-essential amino acids, nM Na-pyruvate, 15% FCS and 500 U/ml leukaemia inhibitory factor (LIF). Briefly, approximately $10^7$ ES cells resuspended in 0.8 ml phosphate buffered saline (PBS) were subjected to electroporation with 25 μg/ml of linearized expression vector (Joyner, Gene Targeting: A Practical Approach, Oxford University Press, New York, 1993). Five minutes after electroporation, ES cells were plated on petri dishes containing fibroblastic feeder cells previously inactivated by treatment with 100 μg/ml mitomycin C. One day after electroporation, culture medium was changed to medium containing 450 μg/ml 0418. Resistant clones were separately isolated and cultured 14 days after applying the selection medium. Cells were always cultured at 37° C., 5% $CO_2$. These untreated and undifferentiated ES cells were used as control the experiment shown in FIG. 1 (referred to as 'ES' in FIG. 1).

Example 2

Differentiation of ES Cells into Insulin-Producing Cells (Referred to as 'Control' in FIG. 1)

The ES cell line R1 (wild type, 'wt ES' in FIG. 1) and ES cells constitutively expressing Pax4 ('Pax4 ES' in FIG. 1) were cultivated as embryoid bodies (EB) by the hanging drop method, as described in patent application PCT/EP02/04362, published as WO 02/086107 and by Blyszczuk et al., 2003, Proc Natl Aced Sci USA. 100: 998-1003, which are incorporated herein by reference, with media as described below and in Table 2. The embryoid bodies were allowed to form in hanging drop cultures for 2 days and then transferred for three days to suspension cultures in petri dishes. At day 5, EBs were plated separately onto gelatin-coated 6 cm cell culture dishes containing a differentiation medium prepared with a base of Iscove modified Dulbecco's medium. After dissociation and replating at day 14, cells were cultured up to 40 days in the differentiation medium prepared with a base of Dulbecco's modified Eagle medium: Nutrient Mixture F-12 (DMEM/F12).

Example 3

Expression of Pancreas Specific Genes after Differentiation of ES Cells into Insulin-Producing Cells Expression levels of pancreas specific genes was measured by semi-quantitative RT-PCR analysis. Differentiated wild type ES and Pax4 ES cells were collected after embryoid body formation and suspended in lysis buffer (4 M guanidinium thiocyanate, 25 mM sodium citrate, pH 7; 0.5% sarcosyl, 0.1 M beta-mercaptoethanol). Total RNA was isolated by the single step extraction method described by Chomczynski & Sacchi, 1987, Anal. Biochem. 162: 156-159). mRNA was reverse transcribed using PolyT tail primer Oligo d(T)$_{16}$ (Perkin Elmer) (SEQ ID NO: 8) and the resulting cDNA was amplified using oligonucleotide primers complementary and identical to transcripts of beta-cell glucose transporter Glut2 and insulin. The house keeping gene beta-tubulin was used as internal standard. Reverse transcription (RT) was performed with MuLV reverse transcriptase (Perkin Elmer). Multiplex PCRs were carried out using AmpliTaq DNA polymerase (Perkin Elmer) as described in Wobus at al., 1997, supra. mRNA levels of genes encoding Glut2 and insulin were analysed using the Dynalbeads mRNA DIRECT micro kit (Dynal) according to the manufacturer's instructions.

One third of each PCR reaction was separated by electrophorese. Ethidium bromide fluorescence signals of gels were analyzed by a special software (TINA2.08e) The intensity of the ethidium bromide fluorescence signals was determined from the area under the curve for each peak and the data of target genes were plotted as percentage changes in relation to the expression of the housekeeping gene beta-tubulin.

Results show that markers for beta-cell differentiation function were expressed at higher levels in Pax4$^+$ differentiated ES cells than in differentiated wild type ES cells demonstrating that activation of a pancreatic developmental control gene renders differentiation more efficient than for wild type ES cells (FIG. 1), Expression of Glut2 in differentiated stem cells indicates that hormone-producing cells are capable of responding to glucose. Expression of substantial amounts of insulin in differentiated stem cells indicates that differentiated cells show a phenotype similar to beta-cells.

Example 4

Induction of differentiation of insulin-producing cells by Neurturin (referred to as EB+NTN in FIG. 1)

Figure 1A:
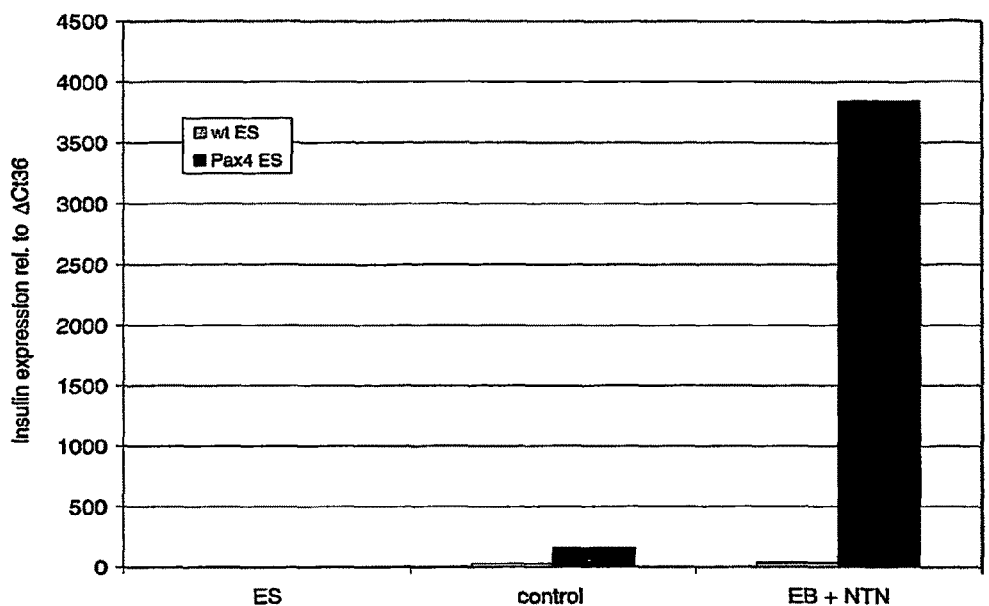
FIG. 1 shows the neurturin dependent induction of the differentiation of insulin producing cells.
Figure 1B:
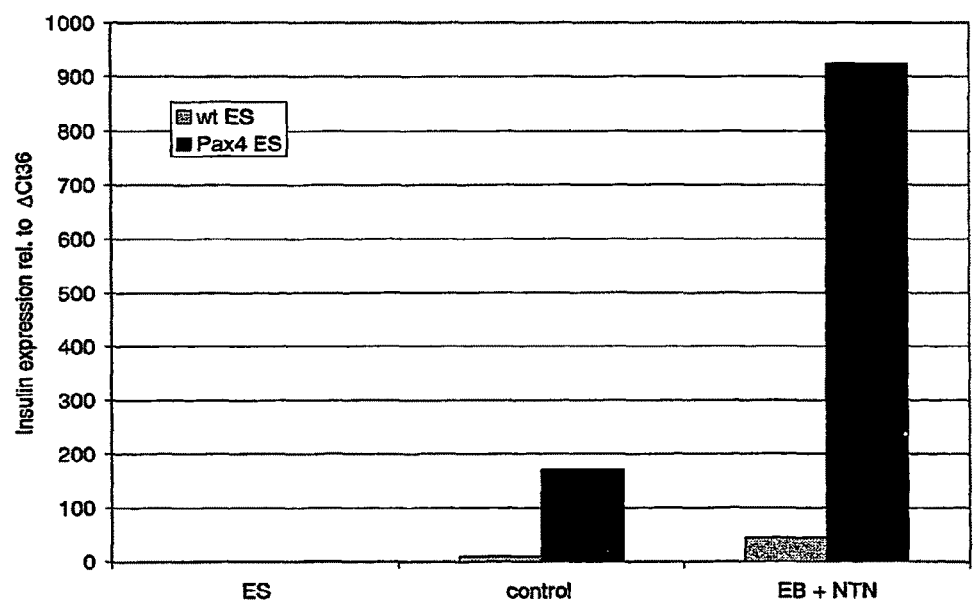
Figure 1C:
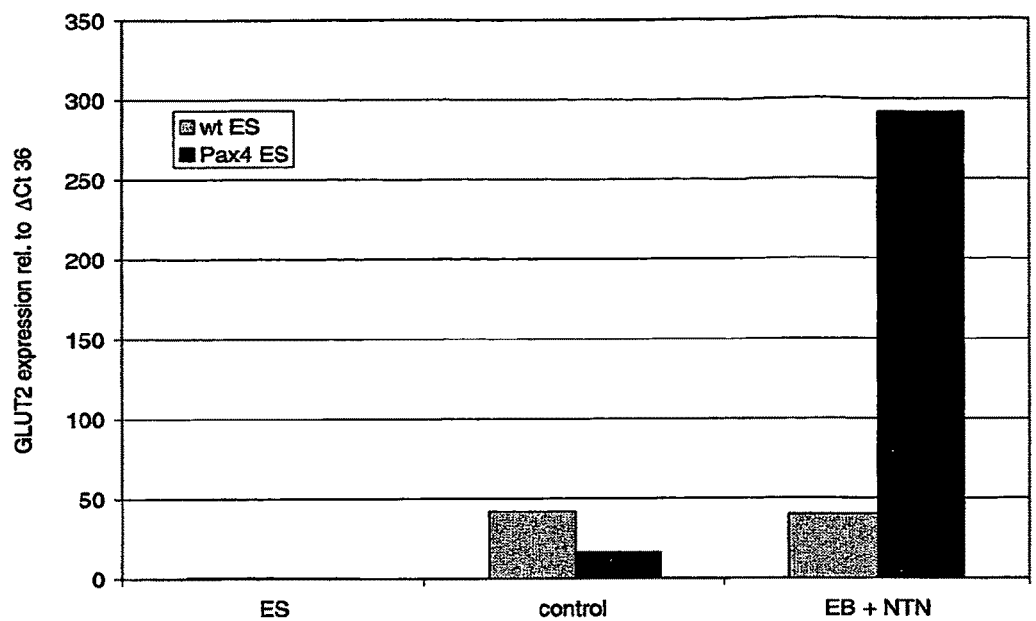
Figure 1D:
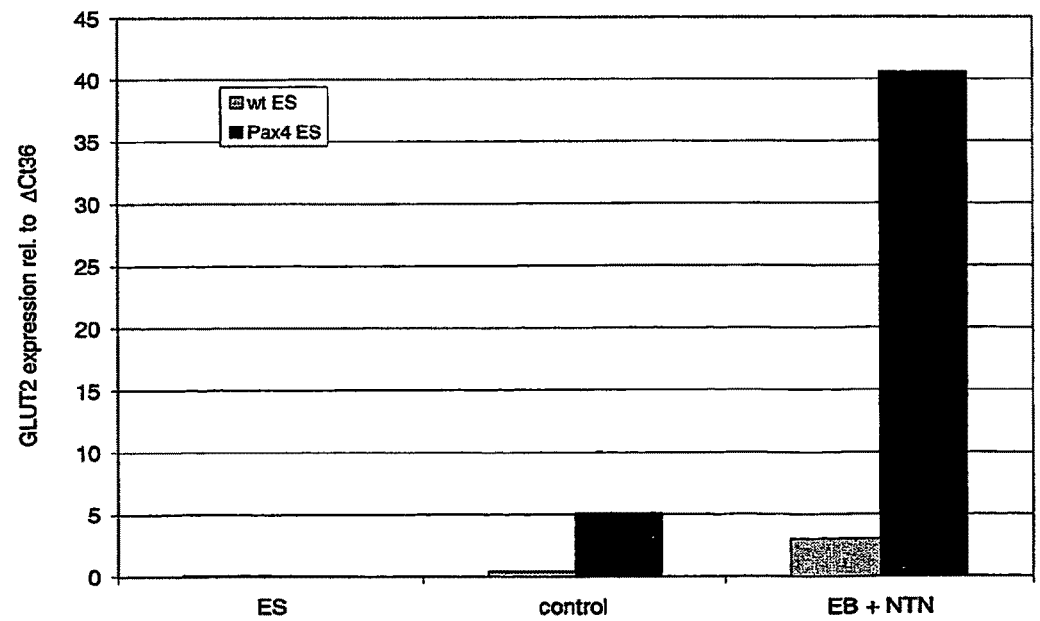

In order to study the effect of neurturin to induce beta-cell differentiation in vitro, we have generated stable mouse embryonic stem (ES) cells expressing Pax4 under the control of the cytomegalovirus (CMV) early promoter/enhancer region as described in Example 1. Pax4 and wild type ES cells were then cultured in hanging drops or spinner cultures to allow the formation of embryoid bodies. Embryoid bodies were formed in the presence of 50 ng/ml of neurturin solution in PBS-01% BSA. Embryoid bodies were subsequently plated, again neurturin was added every second day until day and afterwards enzymatically dissociated, and replated. After dissociation, cells were cultured in a differentiation medium containing various growth factors (see Table 2 for more detail). Neurturin was obtained from RDI Research Diagnostics INC, USA, Order Number RDI-4511. Under such conditions, the expression of insulin was significantly induced by neurturin in two independent examples (FIGS. 1A and 1B). In addition, the addition of neurturin to the differentiation medium did significantly enhance the expression of the glucose transporter Glut-2 in two independent examples (FIGS. 1C and 1D). By comparison, wild type ES cells did not contain any insulin-producing cell at the same stage and only small numbers of Glut-2 expressing cells. These data demonstrate that neurturin can significantly promote and enhance ES cells differentiation into insulin-producing cells compared to wild type ES cells.

The results shown in FIG. 1 clearly demonstrate a significant induction of the differentiation of insulin-producing (FIGS. 1A and 1B) and glucose responsive (FIGS. 1C and 1D) cells, if neurturin is added to embryoid bodies. Thus, neurturin has a strong inductive effect on the differentiation of insulin-producing beta cells.

TABLE 2

Protocol for the induction of differentiation of insulin-producing cells by Neurturin.
Media B1, B2 and B27 supplement, (NA-Niacinamide) are described in Rolletschek et al., 2001, Mech. Dev. 105: 93-104.

| Day | Stage of Cultivation | Medium | Coating and Analysis |
|---|---|---|---|
| 0 | hanging drops (200 cells/drop) | Iscove + 15% FCS addition of Neurturin (NTN) 50 ng/ml | RNA (ES cells) |
| 1 | | | |
| 2 | EBs in suspension | Iscove + 15% FCS + NTN, 50 ng/ml | |
| 3 | | | |
| 4 | plating of EBs | Iscove + 10% FCS + NTN, 50 ng/ml | gelatin coating RNA (EBs) |
| +1 | medium change | B1 medium + NTN, 50 ng/ml | ornithine/laminin coating |
| +2 | | | |
| +3 | medium change | | |
| +4 | | | |
| +5 | medium change | | |
| +6 | | | |
| +7 | medium change | | |
| +8 | dissociation | B2 + B27 + NA + 10% FCS | RNA (1 × 6 cm dish) |
| +9 | medium change | see above, withdraw FCS | |
| +10 | | | |
| +11 | medium change | | |
| +12 | | | |
| +13 | medium change | | |
| +14 | | | |
| +15 | medium change | | |
| +16 | | | |
| +17 | medium change | | |
| +18 | | | |
| +19 | medium change | | |
| +20 | | | |
| +21 | medium change | | |
| +22 | | | |
| +23 | medium change | | |
| +24 | | | |
| +25 | medium change | | Immunofluorescence (IF); RNA |
| +26 | | | |
| +27 | medium change | | |
| +28 | | | IF; RNA |
| +29 | medium change | | |
| +30 | | | |
| +31 | medium change | | |
| +32 | | | IF; RNA |

Example 5

Functional Characterization of the Differentiated Insulin-Producing Cells

One important property of beta-cells is glucose responsive insulin secretion. To test whether the Pax4 derived insulin-producing cells possessed this glucose responsive property, an in vitro glucose responsive assay was performed on the differentiated cells. On the day of the assay, the differentiation medium of 12 or 6 well plate was removed and the cells were washed 3 times with Krebs Ringer Bicarbonate Hepes Buffer (KRBH; 125 mM NaCl, 4.7 mM KCl, 1 mM $CaCl_2$, 1.2 mM $KH_2PO_4$, 1.2 mM $MgSO_4$, 5 mM $NaHCO_3$, 25 mM Hepes, 0.1% BSA) supplemented with 2.8 mM glucose. For pre-incubation cells were incubated in KRBH 4-2.8 mM glucose for 2 hours at 37° C. Afterwards cells were incubated in 750 µl up to 1 ml KRBH+2.8 mM glucose for 1 hour at 37° C. The supernatant was kept for measurement of basal insulin secretion. For the stimulated insulin release 750 µl up to 1 ml KRBH containing 16.7 mM glucose was added to the cells. After 1 hour incubation at 37° C., the KRBH was recovered for measurement of glucose-induced insulin secretion and the cells were extracted with acid-ethanol (see also Irminger, J.-C. et al., 2003, Endocrinology 144: 1368-1379). Insulin levels were determined by an Enzyme-Linked Immunosorbent Assay (ELISA) for mouse insulin (Mercodia) and performed according to the manufacture is recommendations. An alternative medium for proper insulin release was medium based on DMEM with glucose concentration of 1 g/l (Gibco) supplemented with non-essential amino acids (Gibco, stock solution 1:100) and additional factors mentioned above. Such medium can be applied 1 to 6 days before use of the cells.

A basal insulin secretion is expected when both wild type and neurturin induced insulin-producing cells are cultured in low glucose concentrations (2.8 mM). However, the neurturin induced insulin-producing cells highly respond to glucose stimulation. In the presence of high glucose concentrations (16.7 mM), an increase in insulin secretion is expected in neurturin ES derived insulin-producing cells.

Example 6

Transplantation of Pax4 ES Derived Insulin-Producing Cells in STZ Diabetic Mice

The therapeutic potential of neurturin induced insulin-producing cells to improve and cure diabetes can be investigated by transplanting the cells into streptozotocin induced diabetic mice. Streptozotocin is an antibiotic which is cytotoxic to beta-cells when administered at certain dosage (see Rodrigues et al.: Streptozotocin-induced diabetes, in McNeill (ed) Experimental Models of Diabetes, CRC Press LLC, 1999). Its effect is rapid, rendering an animal severely diabetic within 48 hours.

Non-fasted Male BalbC mice were treated with STZ to develop hyperglycaemia after STZ treatment. Mice were considered diabetic if they had a blood glucose level above 10 mmol/l for more than 3 consecutive days. Cells were transplanted under the kidney capsule and into the spleen of animals. The presence of the insulin-producing cells was confirmed by immunohistological analysis of the transplanted tissue. Results are expected to demonstrate that the transplanted cells can normalise blood glucose in diabetic animals.

All publications and patents mentioned in the above specification are herein incorporated by reference. Various modifications and variations of the described method and system of the invention will be apparent to those skilled in the art without departing from the scope and spirit of the invention Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

Example 7

Generation of a mDG770 Transgenic Construct

A complete mDG770 Open Reading Frame (ORF) was cloned under the control of the rat insulin promoter II (Lomedico at al., (1979) Cell 18: 545-558) using the Gateway system (Invitrogen). For the structure of the transgenic construct, see also FIG. 2.

Example 8

Generation of rIP-mDG770 Transgenic Mice

Transgenic construct DNA (see Example 7) was injected into C57/BL6×CBA embryos (Harlan Winkelmann, Borchen, Germany) using standard techniques (see, for example, Brinster at al. (1985), Proc. Natl. Acad. Sci. USA 82: 4438-4442). The mDG770 transgene (see Example 7) was expressed under the control of the rat insulin promoter II (Lomedico at al., supra) using techniques known to those skilled in the art (for example, see, Gunnig at al. (1987), Proc. Natl. Acad. Sci. USA 84, 4831-4835). Using this technique, several independent founderlines were generated.

Example 9

Genotype Analysis of rIP-mDG770 Transgenic Mice

Genotyping was performed by PCR using genomic DNA isolated from the tail tip. To detect the mDG770 transgene a transgene specific forward primer (5' tgc tat ctg tct gga tgt gcc 3' (SEQ ID NO: 1) and a mDG770 transgene specific reverse primer (5' aag gac acc tcg tcc tca tag 3' (SEQ ID NO: 2)) was used.

Example 10 mDG770 Expression Analysis via TaqMan Analysis

The expression of the mDG770 transgene in islets was monitored by TaqMan analysis. For this analysis, 25 ng cDNA derived from pancreatic islet RNA isolated from transgenic mice and their littermates and a mDG770 specific primer/probe pair were used to detect endogenous as well as transgenic mDG770 expression (mDG770-1 forward primer: 5' GCC TAT GAG GAC GAG GTG TCC 3' (SEQ ID NO: 3), mDG770 reverse primer: 5' AGC TCT TGC AGC GTG TGG T 3' (SEQ ID NO: 4), mDG770 probe: 5' TCC TGG ACG TGC ACA GCC GC 3' (SEQ ID NO: 5). TaqMan analysis was performed using standard techniques known to those skilled in the art. Ectopic transgene expression was detected in 3 of 4 rIP-mDG770 transgenic founderlines analysed. The two founderlines showing highest transgene expression levels were used for further analysis. For the level of mDG70 expression in islets of a transgenic animal compared to a Wild-type animal, see also FIG. 3.

Example 11

Analytical procedures performed in mDG770 transgenic mice 3 to 6 mice were housed per cage and were provided with food ad libitum. Metabolic blood parameters were determined using venous blood isolated from tail vein or via retroorbital bleeding. Blood glucose values were determined using One Touch blood glucose meters (LifeScan, Germany), mDG770 transgenic mice exhibit reduced random fed blood glucose levels (rIP-mDG770), compared to wild type (wt) mice, see also FIG. 4.

The invention claimed is:

1. A method for lowering blood glucose levels in a mammal having impaired beta cell function, comprising administering neurturin product to the mammal in an amount sufficient to increase neurturin concentration relative to an untreated mammal having impaired beta cell function, wherein blood glucose levels in the mammal administered the neurturin product are lowered; wherein the biologically active neurturin product comprises a biologically active neurturin polypeptide; wherein the biologically active neurturin polypeptide is capable of dimerizing with another neurturin polypeptide; and wherein the neurturin polypeptide shares at least 90% sequence identity with:

a) the human neurturin precursor protein having the amino acid sequence set forth in SEQ ID NO: 7; or b) the mature neurturin protein product that results from the cleavage of the human neurturin protein precursor having an amino acid sequence set forth in SEQ ID NO: 7.

2. The method of claim 1, wherein the neurturin product is administered directly to a pancreas.

3. The method of claim 1, wherein the biologically active neurturin polypeptide shares at least 95% sequence identity with:

a) the human neurturin precursor protein having the amino acid sequence set forth in SEQ ID NO: 7; or b) the mature neurturin protein product that results from the cleavage of the human neurturin protein precursor having an amino acid sequence set forth in SEQ ID NO: 7.

4. The method of claim 3, wherein the biologically active neurturin polypeptide shares 100% sequence identity with:

a) the human neurturin precursor protein having the amino acid sequence set forth in SEQ ID NO: 7; or
b) the mature neurturin protein product that results from the cleavage of the human neurturin protein precursor having an amino acid sequence set forth in SEQ ID NO: 7.

5. The method of claim 1, wherein the mammal having impaired beta cell function suffers from diabetes type I.

6. The method of claim 1, wherein the mammal having impaired beta cell function suffers from diabetes type II.

7. The method of claim 1, wherein the mammal having impaired beta cell function suffers from latent autoimmune diabetes in adults.

* * * * *

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      mDG770 transgene specific forward primer

<400> SEQUENCE: 1
tgctatctgt ctggatgtgc c                                              21

<210> SEQ ID NO 2
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      mDG770 transgene specific reverse primer

<400> SEQUENCE: 2
aaggacacct cgtcctcata g                                         21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      mDG770-1 forward primer

<400> SEQUENCE: 3
gcctatgagg acgaggtgtc c                                         21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      mDG770 reverse primer

<400> SEQUENCE: 4
agctcttgca gcgtgtggt                                            19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      mDG770 probe

<400> SEQUENCE: 5
tcctggacgt gcacagccgc                                           20

<210> SEQ ID NO 6
<211> LENGTH: 594
<212> TYPE: DNA
<213> ORGANISM: Homo sapiens

<400> SEQUENCE: 6
atgcagcgct ggaaggcggc ggccttggcc tcagtgctct gcagctccgt gctgtccatc      60
tggatgtgtc gagagggcct gcttctcagc caccgcctcg gacctgcgct ggtcccctg     120 caccgcctgc ctcgaaccct ggacgcccgg attgcccgcc tggcccagta ccgtgcactc     180
ctgcaggggg ccccggatgc gatggagctg cgcgagctga cgcccggggc tgggcggccc     240
ccaggtccgc gccgtcgggc ggggccccgg cggcggcgcg cgcgtgcgcg gttggggggcg     300 cggccttgcg ggctgcgcga gctggaggtg cgcgtgagcg agctgggcct gggctacgcg     360
tccgacgaga cggtgctgtt ccgctactgc gcaggcgcct gcgaggctgc cgcgcgcgtc     420
tacgacctcg ggctgcgacg actgcgccag cggcggcgcc tgcggcggga gcgggtgcgc     480
gcgcagccct gctgccgccc gacggcctac gaggacgagg tgtccttcct ggacgcgcac     540
agccgctacc acacggtgca cgagctgtcg gcgcgcgagt gcgcctgcgt gtga         594

<210> SEQ ID NO 7
```

```
<211> LENGTH: 197
<212> TYPE: PRT
<213> ORGANISM: Homo sapiens

<400> SEQUENCE: 7

Met Gln Arg Trp Lys Ala Ala Leu Ala Ser Val Leu Cys Ser Ser
1               5                   10                  15

Val Leu Ser Ile Trp Met Cys Arg Glu Gly Leu Leu Leu Ser His Arg
                20                  25                  30

Leu Gly Pro Ala Leu Val Pro Leu His Arg Leu Pro Arg Thr Leu Asp
            35                  40                  45

Ala Arg Ile Ala Arg Leu Ala Gln Tyr Arg Ala Leu Leu Gln Gly Ala
        50                  55                  60

Pro Asp Ala Met Glu Leu Arg Glu Leu Thr Pro Trp Ala Gly Arg Pro
65                  70                  75                  80

Pro Gly Pro Arg Arg Arg Ala Gly Pro Arg Arg Arg Arg Ala Arg Ala
                85                  90                  95

Arg Leu Gly Ala Arg Pro Cys Gly Leu Arg Glu Leu Glu Val Arg Val
                100                 105                 110

Ser Glu Leu Gly Leu Gly Tyr Ala Ser Asp Glu Thr Val Leu Phe Arg
            115                 120                 125

Tyr Cys Ala Gly Ala Cys Glu Ala Ala Ala Arg Val Tyr Asp Leu Gly
        130                 135                 140

Leu Arg Arg Leu Arg Gln Arg Arg Arg Leu Arg Arg Glu Arg Val Arg
145                 150                 155                 160

Ala Gln Pro Cys Cys Arg Pro Thr Ala Tyr Glu Asp Glu Val Ser Phe
                165                 170                 175

Leu Asp Ala His Ser Arg Tyr His Thr Val His Glu Leu Ser Ala Arg
            180                 185                 190

Glu Cys Ala Cys Val
            195

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tttttttttt tttttt                                                   16
```